United States Patent
Jacobsen et al.

(10) Patent No.: US 8,614,768 B2
(45) Date of Patent: Dec. 24, 2013

(54) MINIATURIZED IMAGING DEVICE INCLUDING GRIN LENS OPTICALLY COUPLED TO SSID

(75) Inventors: Stephen C. Jacobsen, Salt Lake City, UT (US); David L. Wells, Toronto (CA)

(73) Assignee: Raytheon Company, Waltham, MA (US)

( * ) Notice: Subject to any disclaimer, the term of this patent is extended or adjusted under 35 U.S.C. 154(b) by 344 days.

(21) Appl. No.: 12/792,562

(22) Filed: Jun. 2, 2010

(65) Prior Publication Data

US 2011/0137117 A1 Jun. 9, 2011

Related U.S. Application Data

(63) Continuation of application No. 10/391,489, filed on Mar. 17, 2003, now abandoned.

(60) Provisional application No. 60/365,561, filed on Mar. 18, 2002, provisional application No. 60/365,692, filed on Mar. 18, 2002, provisional application No. 60/431,261, filed on Dec. 6, 2002.

(51) Int. Cl.
*H04N 5/68* (2006.01)
(52) U.S. Cl.
USPC .............................................. 348/379; 348/77
(58) Field of Classification Search
USPC ............. 348/45, 65–77, 82, 84, 85, 203, 335, 348/340, 344, 369, 370, 373
See application file for complete search history.

(56) References Cited

U.S. PATENT DOCUMENTS

| | | | |
|---|---|---|---|
| 3,817,635 A | 6/1974 | Kawahara | |
| 3,856,000 A | 12/1974 | Chikama | |
| 3,886,933 A * | 6/1975 | Mori et al. | 600/135 |
| 3,918,438 A * | 11/1975 | Hayamizu et al. | 600/168 |
| 3,971,065 A | 7/1976 | Bayer | |
| 4,277,168 A * | 7/1981 | Oku | 356/138 |
| 4,283,115 A | 8/1981 | Fraissl | |
| 4,403,985 A | 9/1983 | Boretos | |
| 4,475,902 A | 10/1984 | Schubert | |
| 4,487,206 A | 12/1984 | Aagard | |
| 4,491,865 A | 1/1985 | Danna et al. | |
| 4,515,444 A | 5/1985 | Prescott et al. | |

(Continued)

FOREIGN PATENT DOCUMENTS

CN 1481753 3/2004
DE 197 42 973 4/1998

(Continued)

OTHER PUBLICATIONS

PCT Application PCT/US2010/051188; filed Oct. 1, 2010; Stephen C. Jacobsen; International Search Report mailed Jul. 13, 2011.

(Continued)

*Primary Examiner* — Aung S Moe
*Assistant Examiner* — Chriss Yoder, III
(74) *Attorney, Agent, or Firm* — Thorpe North & Western LLP

(57) ABSTRACT

A miniaturized imaging device and method of viewing small luminal cavities are described. The imaging device can be used as part of a catheter, and can include a solid state imaging device (SSID) including an imaging array, and a graduated refractive index (GRIN) lens optically coupled to the imaging array of the SSID.

20 Claims, 8 Drawing Sheets

(56) References Cited

U.S. PATENT DOCUMENTS

| | | |
|---|---|---|
| 4,573,450 A | 3/1986 | Arakawa |
| 4,585,349 A | 4/1986 | Gross et al. |
| 4,588,294 A | 5/1986 | Siegmund |
| 4,593,313 A | 6/1986 | Nagasaki et al. |
| 4,594,613 A | 6/1986 | Shinbori et al. |
| 4,600,831 A | 7/1986 | Hutley |
| 4,604,992 A | 8/1986 | Sato |
| 4,620,534 A | 11/1986 | Zartman |
| 4,621,284 A | 11/1986 | Nishioka et al. |
| 4,622,954 A | 11/1986 | Arakawa et al. |
| 4,641,927 A | 2/1987 | Prescott et al. |
| 4,646,724 A | 3/1987 | Sato et al. |
| 4,672,218 A | 6/1987 | Chrisman et al. |
| 4,706,118 A | 11/1987 | Kato et al. |
| 4,707,134 A | 11/1987 | McLachlan et al. |
| 4,723,843 A | 2/1988 | Zobel |
| 4,725,721 A | 2/1988 | Nakamura |
| 4,745,470 A | 5/1988 | Yabe et al. |
| 4,745,471 A | 5/1988 | Takamura et al. |
| 4,783,591 A | 11/1988 | Sullivan |
| 4,785,815 A * | 11/1988 | Cohen .......................... 606/15 |
| 4,790,624 A * | 12/1988 | Van Hoye et al. ............ 385/118 |
| 4,791,479 A | 12/1988 | Ogiu et al. |
| 4,802,487 A | 2/1989 | Martin et al. |
| 4,803,562 A | 2/1989 | Eino |
| 4,832,003 A | 5/1989 | Yabe |
| 4,843,416 A | 6/1989 | Brower |
| 4,846,785 A | 7/1989 | Cassou et al. |
| 4,859,040 A | 8/1989 | Kitagishi et al. |
| 4,867,137 A | 9/1989 | Takahashi |
| 4,867,138 A | 9/1989 | Kubota et al. |
| 4,867,174 A | 9/1989 | Skribiski |
| 4,880,298 A | 11/1989 | Takada |
| 4,895,138 A | 1/1990 | Yabe |
| 4,916,534 A | 4/1990 | Takhashi et al. |
| 4,926,257 A | 5/1990 | Miyazaki |
| 4,930,880 A | 6/1990 | Miyauchi |
| 4,932,394 A | 6/1990 | Nanaumi |
| 4,934,340 A * | 6/1990 | Ebling et al. ................. 600/151 |
| 4,941,457 A * | 7/1990 | Hasegawa ..................... 600/142 |
| 4,998,807 A | 3/1991 | Uzawa et al. |
| 5,006,928 A | 4/1991 | Kawajiri et al. |
| 5,009,483 A | 4/1991 | Rockwell, III |
| 5,021,888 A | 6/1991 | Kondou et al. |
| 5,032,913 A | 7/1991 | Hattori et al. |
| 5,040,069 A | 8/1991 | Matsumoto et al. |
| 5,061,036 A | 10/1991 | Gordon |
| 5,093,719 A | 3/1992 | Prescott |
| 5,105,269 A | 4/1992 | Nakamura et al. |
| 5,106,387 A | 4/1992 | Kittrell et al. |
| 5,109,859 A | 5/1992 | Jenkins |
| 5,111,804 A | 5/1992 | Funakoshi |
| 5,113,254 A | 5/1992 | Kanno et al. |
| 5,121,213 A | 6/1992 | Nishioka |
| 5,126,369 A | 6/1992 | Wilson et al. |
| 5,126,639 A | 6/1992 | Srivastava |
| 5,130,804 A | 7/1992 | Tamura et al. |
| 5,165,063 A | 11/1992 | Strater et al. |
| 5,166,656 A | 11/1992 | Badihi et al. |
| 5,182,672 A | 1/1993 | Mukai et al. |
| 5,188,093 A | 2/1993 | Lafferty et al. |
| 5,190,523 A | 3/1993 | Lindmayer |
| 5,191,203 A | 3/1993 | McKinley |
| 5,198,894 A | 3/1993 | Hicks |
| 5,209,219 A | 5/1993 | Hollobaugh |
| 5,220,198 A | 6/1993 | Tsuji |
| 5,222,477 A | 6/1993 | Lia |
| 5,228,430 A | 7/1993 | Sakamoto |
| 5,258,834 A | 11/1993 | Tsuji et al. |
| 5,289,434 A | 2/1994 | Berni |
| 5,290,555 A | 3/1994 | Guthauser et al. |
| 5,291,010 A | 3/1994 | Tsuji |
| 5,298,741 A | 3/1994 | Walt et al. |
| 5,304,173 A | 4/1994 | Kittrell et al. |
| 5,305,098 A | 4/1994 | Matsunaka et al. |
| 5,318,024 A | 6/1994 | Kittrell et al. |
| 5,361,166 A | 11/1994 | Atkinson et al. |
| 5,365,268 A | 11/1994 | Minami |
| 5,376,960 A | 12/1994 | Wurster |
| 5,377,047 A | 12/1994 | Broome et al. |
| 5,381,784 A | 1/1995 | Adair |
| 5,396,366 A | 3/1995 | Brown et al. |
| 5,398,685 A | 3/1995 | Wilk et al. |
| 5,402,769 A | 4/1995 | Tsuji |
| 5,430,475 A | 7/1995 | Goto et al. |
| 5,434,615 A | 7/1995 | Matumoto |
| 5,436,655 A | 7/1995 | Hiyama et al. |
| 5,438,975 A | 8/1995 | Miyagi et al. |
| 5,440,669 A | 8/1995 | Rakuljie et al. |
| 5,450,243 A | 9/1995 | Nishioka |
| 5,455,455 A | 10/1995 | Badehi |
| 5,458,612 A | 10/1995 | Chin |
| 5,459,570 A | 10/1995 | Swanson et al. |
| 5,469,841 A | 11/1995 | Kobayashi et al. |
| 5,494,483 A | 2/1996 | Adair |
| 5,512,940 A | 4/1996 | Takasugi et al. |
| 5,517,997 A | 5/1996 | Fontenot |
| 5,531,664 A | 7/1996 | Adachi et al. |
| 5,547,455 A | 8/1996 | McKenna et al. |
| 5,547,906 A | 8/1996 | Badehi |
| 5,594,497 A | 1/1997 | Ahern |
| 5,603,687 A | 2/1997 | Hori et al. |
| 5,621,574 A | 4/1997 | Foo |
| 5,630,788 A | 5/1997 | Forkner et al. |
| 5,647,368 A | 7/1997 | Zeng et al. |
| 5,662,621 A * | 9/1997 | Lafontaine .................... 604/528 |
| 5,673,083 A | 9/1997 | Izumi et al. |
| 5,685,311 A | 11/1997 | Hara |
| 5,693,043 A | 12/1997 | Kittrell et al. |
| 5,704,892 A | 1/1998 | Adair |
| 5,716,323 A | 2/1998 | Lee |
| 5,716,759 A | 2/1998 | Badehi |
| 5,722,403 A | 3/1998 | McGee et al. |
| 5,732,150 A | 3/1998 | Zhou et al. |
| 5,740,808 A | 4/1998 | Panescu et al. |
| 5,749,827 A | 5/1998 | Minami |
| 5,751,340 A | 5/1998 | Strobl et al. |
| 5,752,518 A | 5/1998 | McGee et al. |
| 5,769,792 A | 6/1998 | Palcic et al. |
| 5,772,597 A | 6/1998 | Goldberger et al. |
| 5,776,049 A | 7/1998 | Takahashi |
| 5,783,829 A | 7/1998 | Sealock et al. |
| 5,784,098 A | 7/1998 | Shoji et al. |
| 5,792,984 A | 8/1998 | Bloom |
| 5,800,341 A | 9/1998 | McKenna et al. |
| 5,807,261 A | 9/1998 | Benaron et al. |
| 5,808,665 A | 9/1998 | Green |
| 5,818,644 A * | 10/1998 | Noda ............................. 359/642 |
| 5,827,172 A | 10/1998 | Takahashi et al. |
| 5,840,017 A | 11/1998 | Furusawa et al. |
| 5,846,185 A | 12/1998 | Carollo |
| 5,848,969 A | 12/1998 | Panescu et al. |
| 5,865,729 A | 2/1999 | Meehan et al. |
| 5,870,229 A | 2/1999 | Tsuchida |
| 5,873,816 A | 2/1999 | Kagawa et al. |
| 5,879,285 A | 3/1999 | Ishii |
| 5,904,651 A | 5/1999 | Swanson et al. |
| 5,908,445 A | 6/1999 | Whayne et al. |
| 5,913,817 A | 6/1999 | Lee |
| 5,916,155 A | 6/1999 | Levinson et al. |
| 5,929,900 A | 7/1999 | Yamanaka et al. |
| 5,940,126 A | 8/1999 | Kimura |
| 5,947,894 A | 9/1999 | Chapman et al. |
| 5,951,462 A | 9/1999 | Yamanaka |
| 5,957,849 A | 9/1999 | Munro |
| 5,971,915 A | 10/1999 | Yamamoto et al. |
| 5,973,779 A | 10/1999 | Ansari et al. |
| 5,980,663 A | 11/1999 | Badehi |
| 5,989,185 A | 11/1999 | Miyazaki |
| 5,998,878 A | 12/1999 | Johnson |
| 5,999,327 A | 12/1999 | Nagaoka |
| 6,008,123 A | 12/1999 | Kook et al. |
| 6,014,919 A | 1/2000 | Jacobsen et al. |
| 6,022,758 A | 2/2000 | Badehi |

(56) References Cited

U.S. PATENT DOCUMENTS

| | | |
|---|---|---|
| 6,040,235 A | 3/2000 | Badehi |
| 6,095,970 A | 8/2000 | Hidaka et al. |
| 6,117,707 A | 9/2000 | Badehi |
| 6,118,476 A | 9/2000 | Morito et al. |
| 6,133,637 A | 10/2000 | Hikita et al. |
| 6,134,003 A * | 10/2000 | Tearney et al. ............... 356/479 |
| 6,139,489 A | 10/2000 | Wampler et al. |
| 6,142,930 A | 11/2000 | Ito et al. |
| 6,161,035 A | 12/2000 | Furusawa |
| 6,184,923 B1 | 2/2001 | Miyazaki |
| 6,211,955 B1 | 4/2001 | Basiji et al. |
| 6,261,226 B1 | 7/2001 | McKenna et al. |
| 6,262,855 B1 | 7/2001 | Greisz |
| 6,280,960 B1 | 8/2001 | Carr |
| 6,288,172 B1 | 9/2001 | Goetz et al. |
| 6,319,745 B1 | 11/2001 | Bertin et al. |
| 6,322,498 B1 | 11/2001 | Gravenstein et al. |
| 6,327,096 B1 | 12/2001 | Tsuchida |
| 6,352,503 B1 | 3/2002 | Matsui et al. |
| 6,361,491 B1 * | 3/2002 | Hasegawa et al. ............ 600/175 |
| 6,366,726 B1 | 4/2002 | Wach et al. |
| 6,375,635 B1 | 4/2002 | Moutafis et al. |
| 6,384,397 B1 | 5/2002 | Takiar et al. |
| 6,384,884 B1 | 5/2002 | Nakamura et al. |
| 6,396,116 B1 | 5/2002 | Kelly et al. |
| 6,445,939 B1 | 9/2002 | Swanson et al. |
| 6,456,423 B1 | 9/2002 | Nayfeh et al. |
| 6,471,636 B1 | 10/2002 | Sano et al. |
| 6,485,413 B1 | 11/2002 | Boppart et al. |
| 6,522,913 B2 | 2/2003 | Swanson et al. |
| 6,533,722 B2 | 3/2003 | Nakashima |
| 6,537,205 B1 | 3/2003 | Smith |
| 6,552,796 B2 | 4/2003 | Magnin et al. |
| 6,561,972 B2 | 5/2003 | Ooshima et al. |
| 6,570,659 B2 | 5/2003 | Schmitt |
| 6,573,950 B1 | 6/2003 | Hirata et al. |
| 6,585,717 B1 * | 7/2003 | Wittenberger et al. ....... 604/523 |
| 6,595,913 B2 | 7/2003 | Takahashi |
| 6,618,614 B1 | 9/2003 | Chance |
| 6,622,367 B1 | 9/2003 | Bolduc et al. |
| 6,643,071 B2 | 11/2003 | Schnitzer |
| 6,658,279 B2 | 12/2003 | Swanson et al. |
| 6,659,941 B2 | 12/2003 | Weber et al. |
| 6,695,787 B2 | 2/2004 | Hogendijk et al. |
| 6,710,919 B1 | 3/2004 | Clausen |
| 6,719,686 B2 | 4/2004 | Coakley et al. |
| 6,727,313 B2 | 4/2004 | Zhou et al. |
| 6,761,684 B1 | 7/2004 | Speier |
| 6,785,048 B2 | 8/2004 | Yamaguchi et al. |
| 6,826,422 B1 | 11/2004 | Modell et al. |
| 6,827,683 B2 | 12/2004 | Otawara |
| 6,833,916 B2 | 12/2004 | Osipchuk et al. |
| 6,834,158 B1 | 12/2004 | Templeton |
| 6,842,288 B1 | 1/2005 | Liu et al. |
| 6,850,659 B2 | 2/2005 | Han |
| 6,879,851 B2 | 4/2005 | McNamara et al. |
| 6,881,448 B1 | 4/2005 | Hattori |
| 6,891,984 B2 | 5/2005 | Petersen et al. |
| 6,893,432 B2 | 5/2005 | Intintoli et al. |
| 6,894,729 B2 | 5/2005 | Hirata et al. |
| 6,898,458 B2 | 5/2005 | Zeng et al. |
| 6,900,913 B2 | 5/2005 | Chen |
| 6,930,705 B2 | 8/2005 | Tanaka |
| 6,937,268 B2 | 8/2005 | Ogawa |
| 6,939,348 B2 | 9/2005 | Malecki et al. |
| 6,941,041 B2 | 9/2005 | Yamaguchi et al. |
| 6,944,204 B2 | 9/2005 | Zhou et al. |
| 6,953,432 B2 | 10/2005 | Schiefer |
| 6,956,624 B2 | 10/2005 | Hirata et al. |
| 6,960,165 B2 | 11/2005 | Ueno et al. |
| 6,982,740 B2 | 1/2006 | Adair et al. |
| 6,990,271 B2 | 1/2006 | Gafsi et al. |
| 7,030,904 B2 | 4/2006 | Adair et al. |
| 7,033,317 B2 | 4/2006 | Pruitt |
| 7,058,294 B2 | 6/2006 | Nakahara |
| 7,075,576 B2 | 7/2006 | Creasey et al. |
| 7,081,927 B2 | 7/2006 | Hirata et al. |
| 7,091,500 B2 | 8/2006 | Schnitzer |
| 7,098,871 B1 | 8/2006 | Tegreene et al. |
| 7,108,657 B2 | 9/2006 | Irion et al. |
| 7,153,299 B1 | 12/2006 | Tu et al. |
| 7,165,552 B2 | 1/2007 | Deem et al. |
| 7,166,537 B2 | 1/2007 | Jacobsen et al. |
| 7,167,317 B2 | 1/2007 | Jung et al. |
| 7,186,251 B2 | 3/2007 | Malecki et al. |
| 7,218,822 B2 | 5/2007 | Treado et al. |
| 7,221,388 B2 | 5/2007 | Sudo et al. |
| 7,234,816 B2 | 6/2007 | Bruzzone et al. |
| 7,247,847 B2 | 7/2007 | Webb et al. |
| 7,304,310 B1 | 12/2007 | Shortt et al. |
| 7,393,321 B2 | 7/2008 | Doguchi et al. |
| 7,420,675 B2 | 9/2008 | Giakos |
| 7,511,891 B2 | 3/2009 | Messerschmidt |
| 7,554,597 B2 | 6/2009 | Scherling |
| 7,591,780 B2 | 9/2009 | Jacobsen |
| 7,629,659 B2 | 12/2009 | Jacobsen |
| 7,787,939 B2 | 8/2010 | Jacobsen et al. |
| 7,823,215 B2 | 10/2010 | Giakos |
| 7,835,074 B2 | 11/2010 | Jacobsen et al. |
| 7,901,870 B1 | 3/2011 | Wach |
| 2001/0007051 A1 | 7/2001 | Nakashima |
| 2001/0007511 A1 | 7/2001 | Minami et al. |
| 2001/0024848 A1 | 9/2001 | Nakamura |
| 2001/0049509 A1 | 12/2001 | Sekine et al. |
| 2002/0007110 A1 | 1/2002 | Irion |
| 2002/0080248 A1 | 6/2002 | Adair et al. |
| 2002/0109774 A1 | 8/2002 | Meron et al. |
| 2002/0111534 A1 | 8/2002 | Suzuki et al. |
| 2002/0166946 A1 | 11/2002 | Iizuka et al. |
| 2002/0188204 A1 | 12/2002 | McNamara |
| 2002/0193660 A1 | 12/2002 | Weber |
| 2003/0071342 A1 | 4/2003 | Honda et al. |
| 2003/0092995 A1 | 5/2003 | Thompson |
| 2003/0114732 A1 | 6/2003 | Webler et al. |
| 2003/0197812 A1 | 10/2003 | Hirata et al. |
| 2003/0199761 A1 * | 10/2003 | Yock ............................ 600/435 |
| 2003/0202127 A1 | 10/2003 | Hirata et al. |
| 2003/0220574 A1 | 11/2003 | Markus |
| 2003/0222325 A1 | 12/2003 | Jacobsen |
| 2004/0015049 A1 | 1/2004 | Zaar |
| 2004/0017961 A1 | 1/2004 | Petersen et al. |
| 2004/0059204 A1 | 3/2004 | Marshall |
| 2004/0097804 A1 | 5/2004 | Sobe |
| 2004/0115955 A1 | 6/2004 | Motoyama et al. |
| 2004/0181148 A1 | 9/2004 | Uchiyama et al. |
| 2004/0225222 A1 | 11/2004 | Zeng et al. |
| 2005/0054902 A1 | 3/2005 | Konno |
| 2005/0065504 A1 | 3/2005 | Melsky et al. |
| 2005/0084229 A1 | 4/2005 | Babbitt et al. |
| 2005/0088576 A1 | 4/2005 | Hirata et al. |
| 2005/0099824 A1 | 5/2005 | Dowling et al. |
| 2005/0124875 A1 | 6/2005 | Kawano et al. |
| 2005/0152421 A1 | 7/2005 | Fujitani |
| 2005/0154277 A1 | 7/2005 | Tang et al. |
| 2005/0158899 A1 | 7/2005 | Jacobsen et al. |
| 2005/0174649 A1 | 8/2005 | Okada et al. |
| 2005/0187568 A1 | 8/2005 | Klenk et al. |
| 2005/0197534 A1 | 9/2005 | Barbato et al. |
| 2005/0231718 A1 | 10/2005 | Goodall et al. |
| 2005/0234345 A1 | 10/2005 | Yang |
| 2005/0264813 A1 | 12/2005 | Giakos |
| 2005/0267340 A1 | 12/2005 | Ishihara et al. |
| 2005/0288555 A1 | 12/2005 | Binmoeller |
| 2006/0009682 A1 | 1/2006 | Nagasawa et al. |
| 2006/0013593 A1 | 1/2006 | Yokoo et al. |
| 2006/0017928 A1 | 1/2006 | Crowther |
| 2006/0051036 A1 | 3/2006 | Treado |
| 2006/0069312 A1 | 3/2006 | O'Connor |
| 2006/0079835 A1 | 4/2006 | Frassica |
| 2006/0106283 A1 | 5/2006 | Wallace et al. |
| 2006/0142700 A1 | 6/2006 | Sobelman et al. |
| 2006/0146172 A1 | 7/2006 | Jacobsen et al. |
| 2006/0161048 A1 | 7/2006 | Squicciarini |
| 2006/0181774 A1 | 8/2006 | Ojima et al. |

(56) References Cited

U.S. PATENT DOCUMENTS

| | | |
|---|---|---|
| 2006/0252994 A1 | 11/2006 | Ratnakar |
| 2006/0253088 A1 | 11/2006 | Chow et al. |
| 2007/0010709 A1 | 1/2007 | Reinschke |
| 2007/0032796 A1 | 2/2007 | Chin-Chen et al. |
| 2007/0073321 A1 | 3/2007 | Mikkaichi et al. |
| 2007/0083232 A1 | 4/2007 | Lee |
| 2007/0088276 A1 | 4/2007 | Stubbs et al. |
| 2007/0135803 A1 | 6/2007 | Belson |
| 2007/0146887 A1 | 6/2007 | Ikeda et al. |
| 2007/0208252 A1 | 9/2007 | Makower |
| 2007/0228300 A1 | 10/2007 | Smith |
| 2007/0233187 A1 | 10/2007 | Lobello |
| 2007/0239066 A1 | 10/2007 | Laham et al. |
| 2007/0255392 A1 | 11/2007 | Johnson |
| 2007/0293727 A1 | 12/2007 | Goldfarb et al. |
| 2008/0045794 A1 | 2/2008 | Belson |
| 2008/0071141 A1 | 3/2008 | Gattani et al. |
| 2008/0094326 A1 | 4/2008 | Yamaki et al. |
| 2008/0114309 A1 | 5/2008 | Zuckerman |
| 2008/0177141 A1 | 7/2008 | Wu et al. |
| 2008/0183080 A1 | 7/2008 | Abraham |
| 2008/0188767 A1 | 8/2008 | Oaki et al. |
| 2008/0227893 A1 | 9/2008 | Tamori et al. |
| 2008/0267562 A1 | 10/2008 | Wang et al. |
| 2009/0027765 A1 | 1/2009 | Kamijima |
| 2009/0036764 A1 | 2/2009 | Rivas et al. |
| 2009/0054791 A1 | 2/2009 | Flusberg |
| 2009/0082626 A1 | 3/2009 | Ichimura et al. |
| 2009/0119808 A1 | 5/2009 | Giakos |
| 2009/0137928 A1 | 5/2009 | Quick et al. |
| 2009/0143645 A1 | 6/2009 | Matthes |
| 2009/0156899 A1 | 6/2009 | Konishi |
| 2009/0180197 A1 | 7/2009 | Jacobsen et al. |
| 2009/0234325 A1 | 9/2009 | Rozenberg et al. |
| 2009/0287048 A1 | 11/2009 | Jacobson et al. |
| 2010/0085567 A1 | 4/2010 | Dottery et al. |
| 2010/0106134 A1 | 4/2010 | Jolly et al. |
| 2010/0134872 A1 | 6/2010 | Johnson et al. |
| 2010/0171821 A1 | 7/2010 | Jacobsen et al. |
| 2010/0248178 A1 | 9/2010 | Nahlieli |
| 2011/0204265 A1 | 8/2011 | Smith et al. |

FOREIGN PATENT DOCUMENTS

| | | |
|---|---|---|
| DE | 19859434 | 7/2000 |
| EP | 0482997 | 4/1992 |
| EP | 0550 995 | 7/1993 |
| EP | 0639043 | 2/1995 |
| EP | 0681809 | 11/1995 |
| EP | 1104182 | 5/2001 |
| EP | 1195130 | 4/2002 |
| EP | 1477104 | 11/2004 |
| EP | 1626436 | 2/2006 |
| EP | 1880656 | 1/2008 |
| JP | 58-046924 | 3/1983 |
| JP | 63-155115 | 6/1988 |
| JP | H05-039501 | 2/1993 |
| JP | 5 -049602 | 3/1993 |
| JP | H07-148105 | 6/1995 |
| JP | H07-222712 | 8/1995 |
| JP | 08-076028 | 3/1996 |
| JP | 08084700 | 4/1996 |
| JP | H09-021963 | 1/1997 |
| JP | 11 137512 | 5/1999 |
| JP | 2001/314365 | 11/2001 |
| JP | 2004/329700 | 11/2004 |
| JP | 2005334462 | 8/2005 |
| JP | 2006/162418 | 6/2006 |
| JP | 2006/320369 | 11/2006 |
| JP | 2007-167387 | 7/2007 |
| JP | 2007/312290 | 11/2007 |
| JP | 2009/067946 | 4/2009 |
| KR | 10-20080027935 | 3/2008 |
| WO | WO 98/38907 | 9/1998 |
| WO | WO 99/40624 | 8/1999 |
| WO | WO 00/54033 | 9/2000 |
| WO | WO 03/081831 | 10/2003 |
| WO | WO 2006/060777 | 6/2006 |
| WO | WO 2007/138889 | 12/2007 |

OTHER PUBLICATIONS

Xie et al; GRIN Lens Rod Based Probe for Endoscopic Spectral Domain Optical Coherence Tomography with Fast Dynamic Focus Tracking; Optics Express; Apr. 17, 2006; 9 pages; vol. 14, No. 8.

Xuting Technologies Co., Ltd.; http://www.xutingby.com/en/products/glinfo.htm; as accessed May 1, 2008; 5 pages.

Frequency; Wikipedia, The Free Encyclopedia; http://en.wikipedia.org.wiki/Frequency; as accessed May 9, 2008; 4 pages.

Introduction to Gradient Index Optics; http://grintech.de/e_main_grin.htm; as accessed May 1, 2008; 7 pages.

Gradient Index (GRIN) Lenses; Grin Tech; 2 pages; The Applicant believes the year of publication of this article is prior to the effective US filing date of this patent application.

Shape Memory Polymers—Biodegradable Sutures; http://www.azom.com/details.asp?ArticleID=1542; as accessed Nov. 6, 2007; 4 pages.

Surgical Needles for Use With Sutures; Wikipedia, The Free Encyclopedia; as accessed Nov. 6, 2007; 6 pages.

Harder et al; Against the Migraine; Science News Online; http://www.sciencenews.org/articles/20050219/bob8.asp; Feb. 19, 2005; 11 pages.

U.S. Appl. No. 12/152,730, filed May 16, 2008; Stephen C. Jacobson; office action issued Sep. 16, 2011.

Boppart, S.A. et al., "Forward-imaging instruments for optical coherence tomography." Optics Letters, Nov. 1, 1997, vol. 22, No. 21, pp. 1618-1620.

Boppart, S.A. et al., "Optical imaging technology in minimally invasive surgery," Surg. Endosc., 1999, vol. 13, pp. 718-722.

Fujimoto, JG et al., "High resolution in vivo intra-arterial imaging with optical coherence tomography," Heart, 1999, vol. 82, pp. 128-133.

Hirofumi Tsuchida et al., "Design of imaging lens systems that use low dispersive radial gradient-index rod," Jpn, J. Appl. Phys. vol. 37 No. 6B, Jun. 30, 1998, pp. 3633-3637.

http://news.thomasnet.com/fullstory/23462 "Near-IR Camera Utilizes CCD Array with Phosphor Coating"; Jun. 11, 2003; 5 pages.

J. Knittel et al., "Endoscope-compatible confocal microscope using a gradient index-lens system" Optics Communications, vol. 188, Issue 5-6, Feb. 2001, pp. 267-273.

Jacobsen, Stephen C., U.S. Appl. No. 10/391,489, filed Mar. 17, 2003.

Jacobsen, Stephen C., U.S. Appl. No. 10/391,490, filed Mar. 17, 2003.

Jacobsen, Stephen C., U.S. Appl. No. 10/391,513, filed Mar. 17, 2003.

Jacobsen, Stephen C., U.S. Appl. No. 11/292,902, filed Dec. 1, 2005.

Jacobsen, Stephen C., U.S. Appl. No. 11/810,702, filed Jun. 5, 2007.

Jacobsen, Stephen C., U.S. Appl. No. 12/008,486, filed Jan. 11, 2008.

Jacobsen, Stephen C., U.S. Appl. No. 12/079,741, filed Mar. 27, 2008.

Jacobsen, Stephen C., U.S. Appl. No. 12/152,730, filed May 16, 2008.

Jacobsen, Stephen C., U.S. Appl. No. 12/487,481, filed Jun. 18, 2009.

Jacobsen, Stephen C., U.S. Appl. No. 12/487,495, filed Jun. 18, 2009.

Jacobsen, Stephen C., U.S. Appl. No. 12/512,188, filed Jul. 30, 2009.

Jacobsen, Stephen C.; U.S. Appl. No. 12/611,776, filed Nov. 3, 2009.

Jacobsen, Stephen C.; U.S. Appl. No. 12/896,731, filed Oct. 1, 2010.

Jacobsen, Stephen C.; U.S. Appl. No. 12/896,732, filed Oct. 1, 2010.

Jacobsen, Stephen C.; U.S. Appl. No. 12/896,737, filed Oct. 1, 2010.

Jacobsen, Stephen C.; U.S. Appl. No. 12/896,743, filed Oct. 1, 2010.

Jacobsen, Stephen C.; U.S. Appl. No. 12/938,672, filed Nov. 3, 2010.

Jacobsen, Stephen C.; U.S. Appl. No. 12/946,442, filed Nov. 15, 2010.

Johansson et al.; "Generation of Turquoise Light by Sum Frequency Mixing of a Diode-Pumped Solid-State Laser and a Laser Diode in Periodically Poled KTP," Optics Express; Oct. 4, 2004; pp. 4935-4940; vol. 12, No. 12.

(56) References Cited

OTHER PUBLICATIONS

Literature from GRIN Tech, "In vivo medical confocal imaging and optical coherence tomography," www.grintech.de, Revision Jun. 2001, pp. 1-3.

Microcam, MINAST Project 5.04, Nov. 11, 1999, http://www.imt.unine.ch/ESPLAB/www/projects/Microcam/, pp. 1-16.

Nguyen, Clark, "Communications Applications of Microelectromechanical Systems," Proceedings, Sensors Expo, May 19-21, 1998, San Jose, CA. pp. 447-455.

Tearney, G.J. et al., "Scanning single-mode fiber optic catheter-endoscope for otpical coherence tomography," Optics Letters, Apr. 1, 1996, vol. 21, No. 7, pp. 543-545.

Zeis, Michael et al., "Color Business Report," ISSN 1055-3339. Jul. 2002, p. 5.

Gaoping et al.; Research on the Measurement of Grin Lens Focused Spot Diameter and Resolution; Applied Optics; 1995; vol. 16, No. 6.

PCT Application PCT/US2010/051200; filed Oct. 1, 2010; Stephen C. Jacobsen; ISR mailed Jun. 3, 2011.

PCT Application PCT/US2010/051198; filed Oct. 1, 2010; Stephen C. Jacobsen; ISR mailed Jun. 3, 2011.

PCT Application PCT/US2010/051192; filed Oct. 1, 2010; Stephen C. Jacobsen; ISR mailed May 30, 2011.

U.S. Appl. No. 12/487,481, filed Jun. 18, 2009; Stephen C. Jacobsen; office action dated Oct. 12, 2012.

U.S. Appl. No. 12/512,188, filed Jul. 30, 2009; Stephen C. Jacobsen; office action dated Nov. 19, 2012.

\* cited by examiner

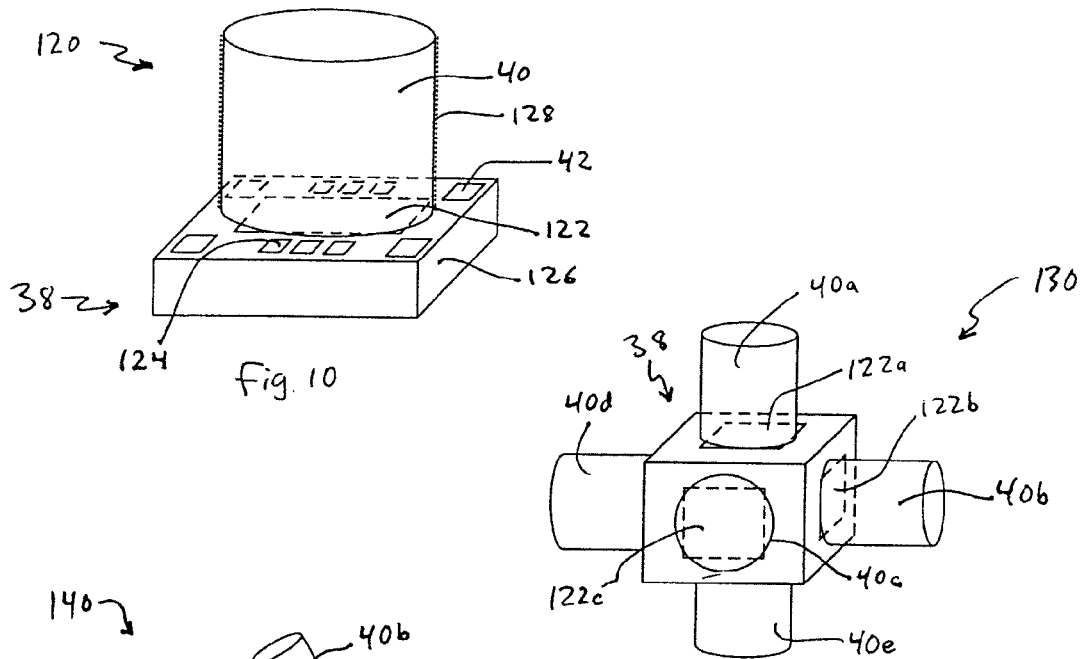
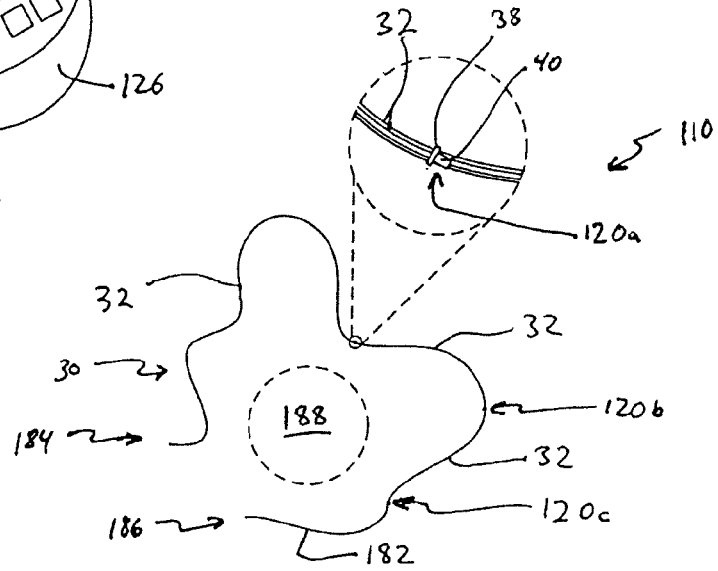

MINIATURIZED IMAGING DEVICE INCLUDING GRIN LENS OPTICALLY COUPLED TO SSID

CLAIM OF PRIORITY

This application is a continuation of U.S. patent application Ser. No. 10/391,489 filed on Mar. 17, 2003 which claims priority to U.S. Provisional Application Nos. 60/365,561 filed Mar. 18, 2002, 60/365,692 filed Mar. 18, 2002, and 60/365,692 filed Dec. 6, 2002, each of which are incorporated herein by reference in their entirety.

FIELD OF THE INVENTION

The invention relates generally to solid state imaging devices (SSIDs). More specifically, the invention relates to miniaturized imaging devices that are particularly suited to viewing beyond small openings and traversing small-diameter areas. These devices can be used for catheter-borne medical imaging within the anatomy of a patient, and are useful for other applications.

BACKGROUND OF THE INVENTION

Small imaging devices that take advantage of advances in integrated circuit imaging technologies are known. Such small imaging devices can be particularly useful in medical diagnostic and treatment applications. Portions of human anatomy previously viewable only by a surgical procedure can be viewed now by a minimally invasive catheterization, provided an imaging device can be made that is small enough to view the target anatomy.

Other uses for very small imaging devices are recognized. For example, such devices can be used and are desirable for surveillance applications, for monitoring of conditions and functions within devices, and for size- and weight-critical imaging needs as are present in aerospace applications, to name a few.

While the present invention has applications in these aforementioned fields and others, the medical imaging application can be used to favorably illustrate unique advantages of the invention. The desirability of providing imaging at sites within the anatomy of living creatures, especially humans, distal of a small orifice or luminal space has long been recognized. A wide variety of types and sub-types of endoscopes have been developed for this purpose.

One advance in imaging technology which has been significant is in the area of SSIDs. Such devices, including the charge-injection device (CID), the charge-coupled device (CCD), and the complementary metal oxide semiconductor (CMOS) device, provide good alternatives to the use of bundled fiber optics, as well as to conventional miniaturized imaging devices used in endoscope applications. However, when considering a design of a catheter-borne imaging device, consideration should be given to the ability of a distal tip of the catheter to flex and bend, without breaking or becoming damaged. This is necessary to accommodate limitations of anatomy to minimize trauma, and to enable steering of the distal tip to a desired location.

Accordingly, there is a desire to manufacture smaller devices that are steerable and provide good image quality for the size.

SUMMARY OF THE INVENTION

It has been recognized that by looking outside conventional devices and techniques, that facilitation of further miniaturization of an imaging device employing SSIDs at a distal end of a catheter or other flexible umbilical can be accomplished. The invention accordingly provides a miniaturized imaging device, comprising an SSID including an imaging array, and a GRIN lens optically coupled to the imaging array of the SSID. A GRIN lens is defined as a graduated refractive index lens.

A method of viewing within or beyond a small luminal opening is also disclosed, comprising steps of (a) inserting a micro camera into a small luminal opening, wherein the microcamera includes a GRIN lens optically coupled to an imaging array of an SSID; (b) illuminating an area around the GRIN lens within or beyond the small luminal opening; (c) receiving light or photon energy in the GRIN lens reflected by contents, e.g., walls or other materials, within or beyond the luminal opening, thereby providing focused light or photon energy at the imaging array; (d) converting the focused light or photon energy to digital data; and (e) processing the digital data for viewing on a monitor remote from the microcamera.

With respect to both the microcamera device and method, the GRIN lens can be substantially cylindrical in shape. In one embodiment, the GRIN lens can have a first flat end for receiving light, a second flat end for passing the light to the imaging array, and an outer curved surface surrounded by an opaque coating or sleeve member to prevent unwanted light from entering the GRIN lens. The GRIN lens can be optically coupled to the imaging array by direct contact between the second flat end and the imaging array. Such direct contact can include a transparent or translucent bonding material, e.g., optically clear UV epoxy, at the interface between the second flat end and the imaging array. Alternatively, the GRIN lens can be optically coupled to the imaging array of the SSID through an intermediate optical device, such as a fiber optic or a color filter.

The SSID can be any solid state imaging device, such as a CCD, a CID, or a CMOS imaging device. The SSID can comprise a conductive pad, or multiple conductive pads, configured for making an electrical connection to the imaging array. The conductive pad(s) provide a means for connecting a conductive line of an umbilical to the SSID. The connection between conductive pads and the conductive line can be through a direct solder joint, wherein no wire bonding between the conductive line and the conductive pads is present. In one embodiment, the umbilical can provide power, ground, clock signal, and output signal with respect to the SSID.

Additionally, the SSID can optionally comprise a pre-processor and an SSID scanning array. The pre-processor can be configured to process image data from the imaging array to produce an image signal transferable over the electrical umbilical. The device can also further comprise a processor and a monitor remote from the SSID, enabling real-time viewing of the image obtained by the SSID.

A utility guide can also be present. The utility guide and/or the SSID itself can be configured for carrying utilities, such as a light source, electrical wires, temperature sensors, force sensors, fluid irrigation or aspiration members, pressure sensors, fiber optics, microforceps, material retrieval tools, drug delivery devices, radiation emitting devices, laser diodes, electric cauterizers, and electric stimulators.

A second imaging array can also be present on a single SSID, or on a second SSID. The second imaging array can provide increased resolution, increased depth perception, stereoscopic viewing, and/or multiple views.

In an alternative embodiment, a miniaturized imaging device can comprise multiple imaging arrays, each carried by an SSID; and multiple lens optically coupled to the multiple imaging arrays, respectively. Preferably, at least one of the multiple lenses is a GRIN lens. In one embodiment, the multiple imaging arrays are carried by a common SSID. In another embodiment, the multiple imaging arrays are carried by separate SSIDs. If the multiple imaging arrays are coplanar, stereoscopic imaging can be facilitated using two lenses coupled to two imaging arrays. If multiple SSIDs and lenses are positioned along a common umbilical, viewing at various positions along an umbilical can occur. Still further, the multiple imaging arrays can be positioned to provide multiple non-parallel views.

Additional features and advantages of the invention will be apparent from the detailed description which follows, taken in conjunction with the accompanying drawings, which together illustrate, by way of example, features of the invention.

BRIEF DESCRIPTION OF THE DRAWINGS

In the accompanying drawings:

FIG. 10 is a perspective view of an SSID optically coupled to a GRIN lens;

FIG. 11 is a perspective view of an exemplary embodiment of an SSID and multiple GRIN lens positioned in an array;

FIG. 12 is a perspective view of another exemplary embodiment of an SSID and multiple GRIN lens positioned in an array;

FIG. 13 is a side view of multiple microcameras positioned along an umbilical as an array;

DETAILED DESCRIPTION OF THE PREFERRED EMBODIMENT(S)

Figure 1:
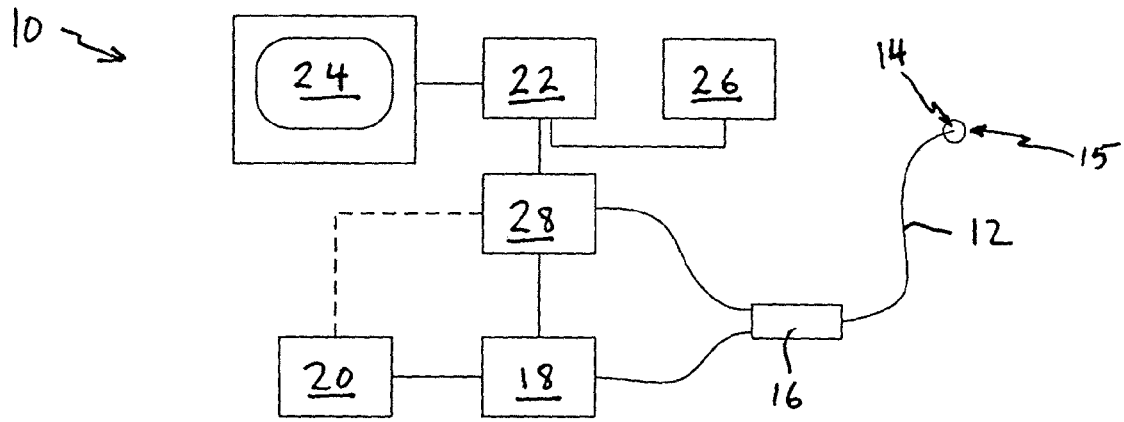
FIG. 1 is a schematic illustration of an exemplary medical imaging system in accordance with principles of the invention.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

It must be noted that, as used in this specification and the appended claims, singular forms of "a," "an," and "the" include plural referents unless the context clearly dictates otherwise.

An "SSID," "solid state imaging device," or "SSID chip" in the exemplary embodiments generally comprises an imaging array or pixel array for gathering image data, and can further comprise conductive pads electrically coupled to the imaging array, which facilitates electrical communication therebetween. In one embodiment, the SSID can comprise a silicon or silicon-like substrate or amorphous silicon thin film transistors (TFT) having features typically manufactured therein. Features can include the imaging array, the conductive pads, metal traces, circuitry, etc. Other integrated circuit components can also be present for desired applications. However, it is not required that all of these components be present, as long as there is a means of gathering visual or photon data, and a means of sending that data to provide a visual image or image reconstruction.

The term "umbilical" can include the collection of utilities that operate the SSID or the micro-camera as a whole. Typically, an umbilical includes a conductive line, such as electrical wire(s) or other conductors, for providing power, ground, clock signal, and output signal with respect to the SSID, though not all of these are strictly required. For example, ground can be provide by another means than through an electrical wire, e.g., to a camera housing such as micromachined tubing, etc. The umbilical can also include other utilities such as a light source, temperature sensors, force sensors, fluid irrigation or aspiration members, pressure sensors, fiber optics, microforceps, material retrieval tools, drug delivery devices, and radiation emitting devices, laser diodes, electric cauterizers, and electric stimulators, for example. Other utilities will also be apparent to those skilled in the art and are thus comprehended by this disclosure.

"GRIN lens" or "graduated refractive index lens" refers to a specialized lens that has a refractive index that is varied radially from a center optical axis to the outer diameter of the lens. In one embodiment, such a lens can be configured in a cylindrical shape, with the optical axis extending from a first flat end to a second flat. Thus, because of the differing refractive index in a radial direction from the optical axis, a lens of this shape can simulate the affects of a more traditionally shaped lens.

With these definitions in mind, reference will now be made to the accompanying drawings, which illustrate, by way of example, embodiments of the invention.

Figure 2:
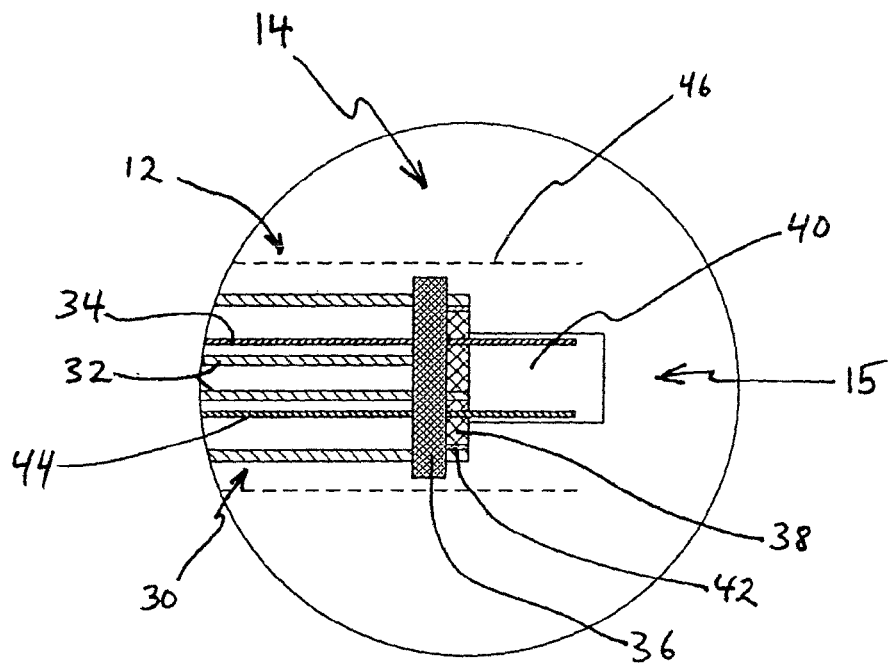
FIG. 2 is a side view of an exemplary embodiment of the present invention, which is an enlarged view of device 14 of FIG. 1.

With reference to FIGS. 1 and 2, the invention is embodied in a medical imaging system 10, including a catheter 12 having an imaging capability by means of an imaging device, shown generally at 14, at a distal tip 15 of the catheter. The system further includes a fitting 16 enabling an imaging fluid, such as a clear saline solution, to be dispensed to the distal tip portion of the catheter from a reservoir 18 to displace body fluids as needed to provide a clearer image. A pump 20 is provided, and is manually actuated by a medical practitioner performing a medical imaging procedure, or can be automated and electronically controlled so as to dispense fluid on demand according to control signals from the practitioner, sensors, or according to software commands.

A processor 22, such as an appropriately programmed computer, is provided to control the imaging system 10 and create an image of anatomy adjacent the distal tip portion 15, within a patient (not shown), displayable on a monitor 24, and storable in a data storage device 26. An interface 28 is provided which supplies power to the imaging device 14 and feeds a digital image signal to the processor based on a signal received from the imaging device via an electrical umbilical 30, including conductive wires 32, a fluid dispenser 34, and a light source 44, through the catheter 12. The interface can also be configured to control the pump 20 based on control signals from the processor or a medical practitioner performing an imaging procedure.

With more specific reference to FIG. 2, the imaging device 14 at the distal tip 15 can include a utility guide 36 for supporting or carrying the umbilical 30, which can include electrical wires 32, a fluid dispenser 34, and a light source 44. Other components that can be carried by the utility guide can include, temperature sensors, force sensors, fluid irrigation or aspiration members, pressure sensors, fiber optics, microforceps, material retrieval tools, drug delivery devices, radiation emitting devices, laser diodes, electric cauterizers, and electric stimulators. The utility guide can also carry an SSID or solid state imaging device 38 that includes an imaging array (not shown) and conductive pads 42 for coupling the electrical wires to the SSID. The light source shown is a fiber optic carried by the utility guide. However, other light sources can be used, such as those carried by the SSID. For example, the SSID can also include light-emitting diodes (LEDs) configured to illuminate the area immediately adjacent the distal tip portion. With the SSID in this configuration, a GRIN lens 40 is shown optically coupled to the imaging array of the SSID.

The GRIN lens 40 can be substantially cylindrical in shape. In one embodiment, the GRIN lens can have a first flat end for receiving light, a second flat end for passing the light to the imaging array, and an outer curved surface surrounded by an opaque coating or sleeve member to prevent unwanted light from entering the GRIN lens. The GRIN lens can be optically coupled to the imaging array by direct contact between the second flat end and the imaging array of the SSID 38. Such direct contact can include an optically transparent or translucent bonding material at the interface between the second flat end and the imaging array. Alternatively, the GRIN lens can be optically coupled to the imaging array of the SSID through an intermediate optical device, such as a fiber optic or a color filter, or any shape optical lens such as a prism or wide angle lens.

The catheter 12 can be configured to be bendable and flexible so as to be steerable within a patient's anatomy and to minimize trauma. For example, the catheter can comprise a micromachined tube 46 at the distal tip portion, and cut-out portions (not shown) can allow for increased flexibility of the tube, and also allow for outflow of an imaging fluid to displace body fluids in the immediate area of the distal tip portion for more clear imaging. Such a micromachined tube can also allow bending to facilitate guiding the catheter to a desired location by selection of desired pathways as the catheter is advanced. Additional details on construction of similar slotted micro-machined tube or segments can be found in U.S. Pat. No. 6,428,489, which is incorporated herein by reference.

The catheter 12 can alternatively comprise an internal tensionable wire (not shown) adjacent one side of the distal tip portion, which when tensioned, causes the distal tip portion 15 to deflect as is known in the art. A combination of deflection and rotation of the distal tip portion of the catheter provides steerability of the device. Another alternative for directability of the distal tip portion is to provide a micro-actuator (not shown) such as an element which expands or contracts upon application of an electrical current signal. Such an element can be substituted for the tension wire, for example.

As will also be appreciated, while the system is illustrated by the exemplary embodiment of a medical imaging system, these arrangements could be used in other devices, such as visual sensors in other devices, surveillance apparatus, and in other applications where a very small imaging device can be useful.

Moreover, with reference to all of the embodiments described herein, the device contemplated can be very small in size, and accordingly the imaging array of the SSID can have a lower pixel count than would otherwise be desirable. As technology advances, pixel size can be reduced, thereby providing clearer images and data. However, when using a lower number of pixels in an imaging array, the resolution of the image provided by the device can be enhanced through software in processing image data received from the SSID. The processor showing in FIG. 1, can be appropriately programmed to further resolve a scanned image from an array of an SSID, for example, based on information received as the SSID is moved slightly, such as from vibration controlled vibration. The processor can analyze how such image data from the imaging array is altered due to the vibration, and can refine the image based on this information.

Figure 3:
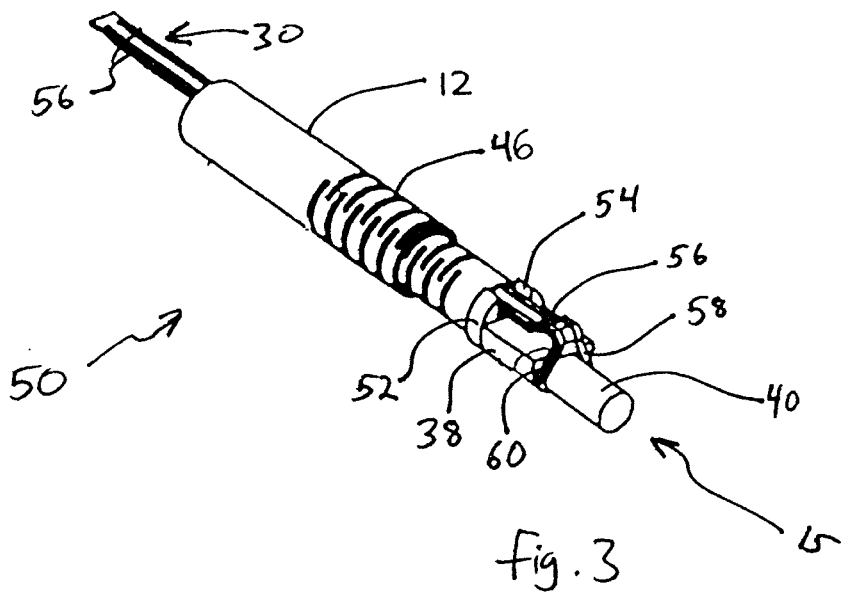
FIG. 3 is a perspective view of another exemplary embodiment of the invention.
Figure 4:
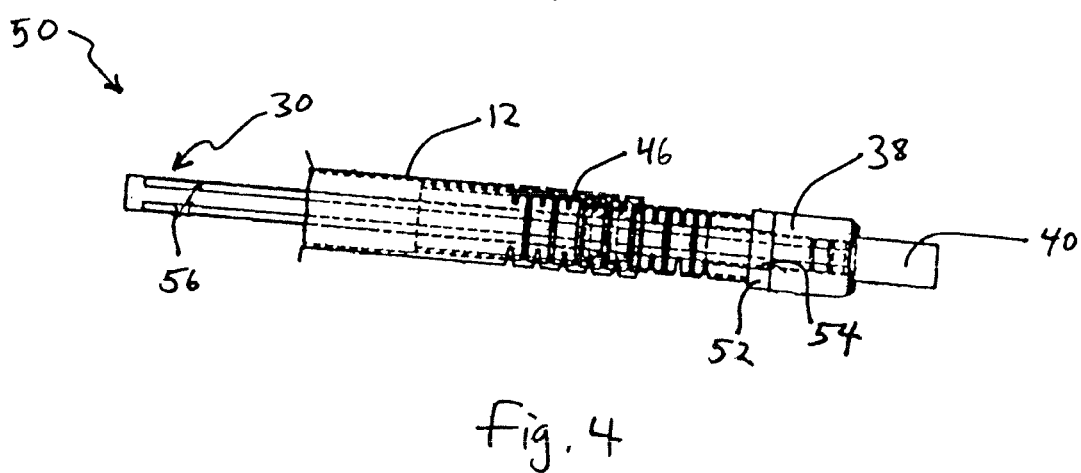
FIG. 4 is a top view of the device of FIG. 3.
Figure 5:
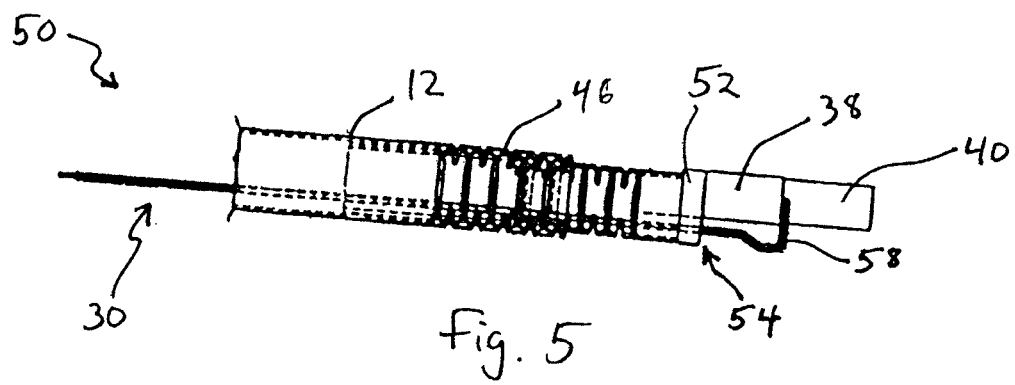
FIG. 5 is a side view of the device of FIG. 3, rotated 90 degrees with respect to FIG. 4.

Turning now to FIGS. 3 to 5, another embodiment of the invention is implemented as shown in system 50, wherein a distal tip portion 15 of a catheter 12 includes lens 40 optically coupled to an SSID 38. Here, the SSID is also electrically bonded to an adaptor 52. The adaptor is carried by micromachined tubing segment 46, and is configured to fit within it at a distal end of the tubing segment. The adaptor has a channel 54 formed therein which allows passage of a conductive strip 56 (which functions similarly as the conductive wires of FIG. 2) of an umbilical 30. The micromachined tubing segment itself is configured to provide telescoping action. This allows the distal tip portion of the catheter to be assembled and then connected easily to the remainder of the catheter. The conductive strip can comprise a ribbon formed of a non-conductive material, such as KAPTON, with conductive traces overlain with a dielectric, and provides an electrical umbilical to the SSID through the adaptor. The conductive strip can be threaded back through the catheter to a fitting (not shown) at its proximal end, as discussed previously. At a distal portion of the conductor strip, individual conductor elements 58, 60 are separated from the non-conductive strip and are bonded to conductive pads (not shown in FIG. 3-5) that are present on the adaptor. Thus, the adaptor provides a power conduit from the umbilical to the SSID.

Figure 6:
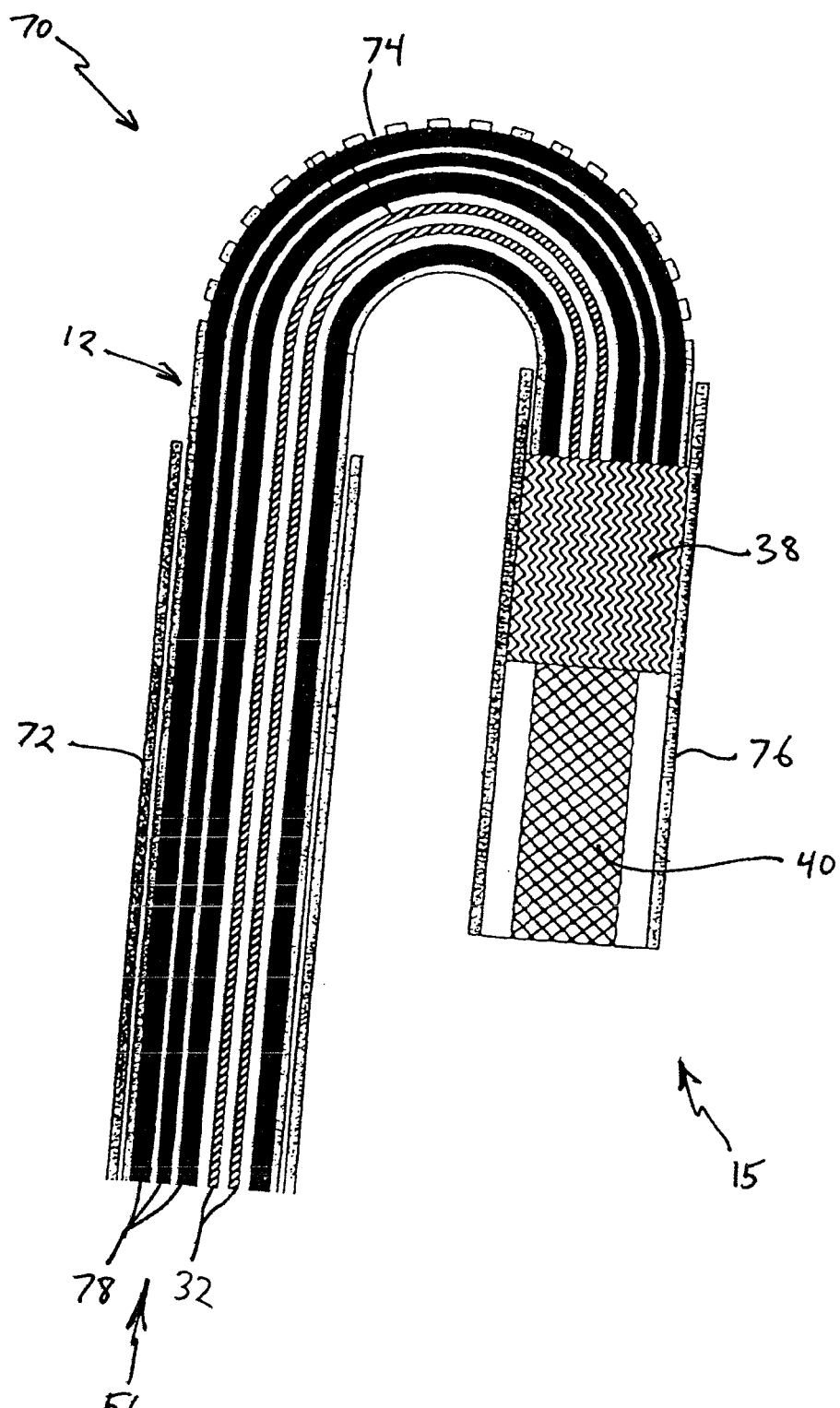
FIG. 6 is a cross sectional view of another exemplary embodiment of the invention.

With reference to FIG. 6, another system is shown generally at 70. In this embodiment, the distal tip 15 of the catheter 12 is shown. An outer sleeve 72 is provided over the outside of the catheter in telescoping fashion. The catheter can be withdrawn into the sleeve at will by differential movement at a proximal end (not shown) of the device. An outer tubing of the catheter can be micromachined to provide a pre-disposition to bend adjacent the SSID 38, for example by micomachining the tubing to provide openings 74 on one side of the tubing and bending the tubing to give it a curved configuration doubling back on itself as shown in the figure. The tip can be directed as desired by pulling the curved portion of the catheter partially, or completely, back into the outer sleeve. In one embodiment, the micro-machined tubing is formed of superelastic material with embedded shape memory capability, such as NiTi alloy so that this can be done repeatedly without the material taking a set. A further outer sleeve 76 is provided adjacent the SSID and GRIN lens 40 to support this structure. A conductive strip 56, including conductive wires 32, can be provided, as described previously.

In another embodiment, tensioning wires 78 can be provided in a lumen within the catheter adjacent a large radius, or outer portion of the catheter 12, which enables directing the tip 15 by providing a tension force tending to straighten out this portion of the catheter. The tension wire is attached to the SSID 38 and extends back through the catheter to a proximal portion where it can be manipulated by a practitioner doing the imaging procedure. The catheter can also include provision for supplying imaging fluid, light, or other utilities, as discussed above.

Figure 7:
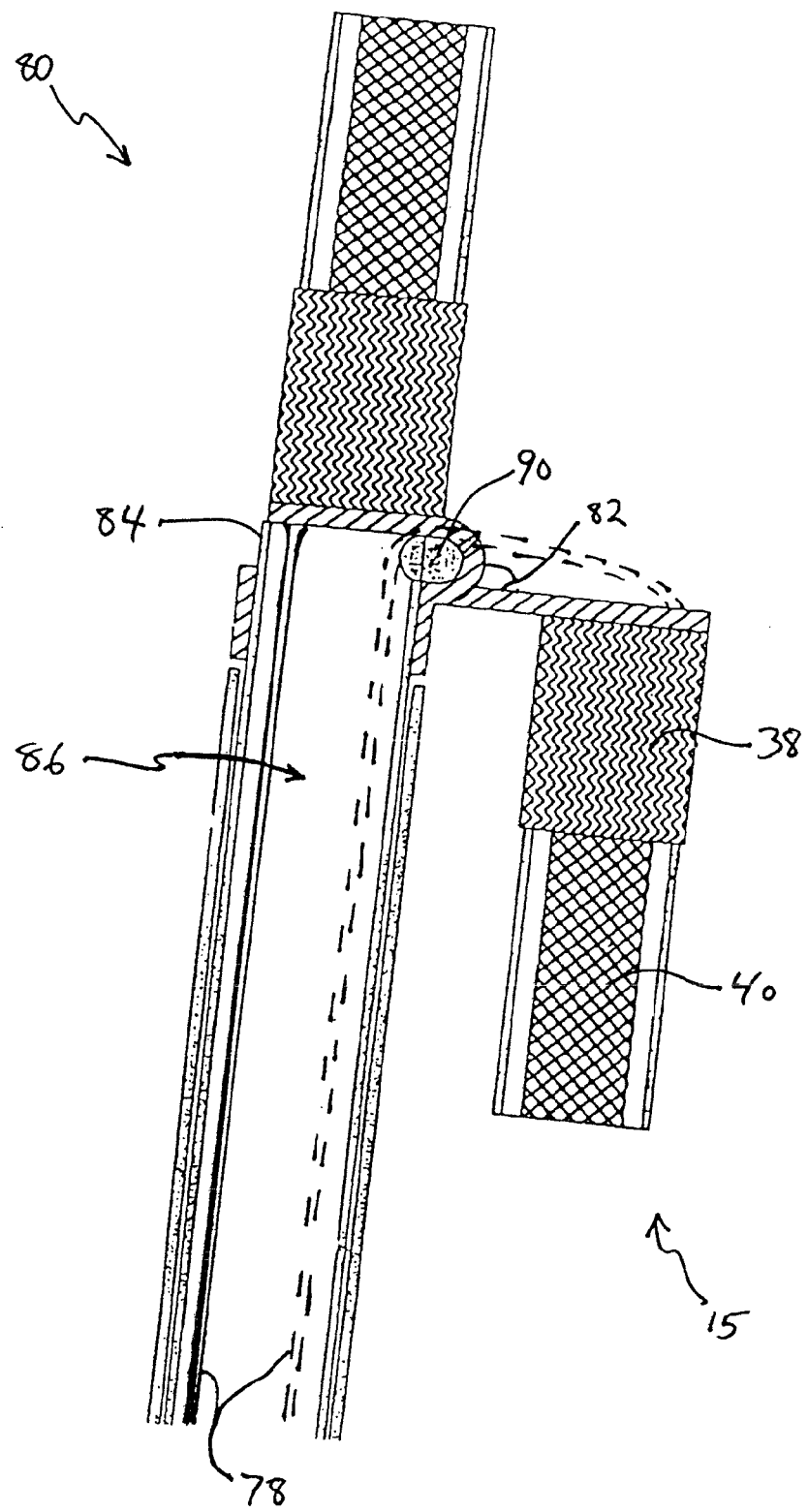
FIG. 7 is a cross sectional view of another exemplary embodiment of the invention.

With reference to FIG. 7, a system shown generally at 80, can comprise an SSID 38 mounted on a hinge 82 formed of super-elastic material with embedded shape memory capability. The hinge is connected to a tube 84 defining an inner lumen 86 of the catheter 12. Tensioning wires 78 are attached to the hinge, and allows the SSID to be directed from a first direction aimed back along the longitudinal axis of the catheter, through 180 degrees, to a second position aiming distally away from the catheter in a direction substantially coincident with the longitudinal axis. This, in combination with rotation of the catheter, allows for directability of the tip. A rounded guide 90 is attached to a distal portion of the tube to provide a radius for the tensioning wires and the hinge so that they do not kink, but deform elastically as shown. Conductive wires (not shown) can be present as describe previously.

Figure 8:
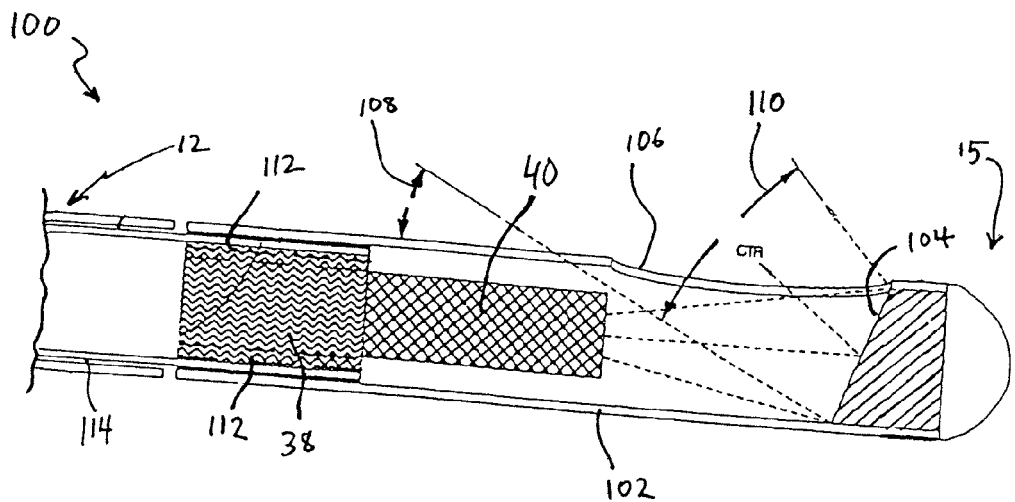
FIG. 8 is a cross sectional view of another exemplary embodiment of the invention in a first configuration.
Figure 9:
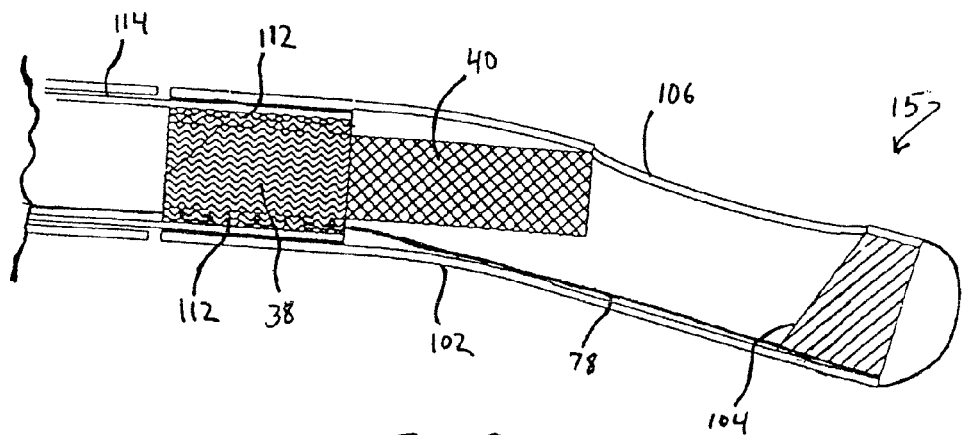
FIG. 9 is a crossectional view of the device of FIG. 8 in a second position view.

Continuing now with reference to FIGS. 8 and 9, an alternative system is shown generally at 100. As shown, control means for directing the catheter 12 and/or directing the field of view of the SSID 38 at the distal tip portion 15 of the catheter is illustrated. A deformable outer sleeve 102 comprising a mirror element 104 at a distal end is provided. An opening 106 adjacent the mirror element and the GRIN lens 40 enables appropriate imaging.

In one configuration state, shown in FIG. 8, the angled surface of the mirror allows a view rearwardly and to the side of the catheter at an angle 108 of about 25 to 50 degrees with respect to a longitudinal axis of the catheter. A field of view 110 based on the configuration and spacing, and angular relationships between the elements can comprise between about 15 and 25 degrees. The SSID can comprise one or more lumens 112 for conveying imaging fluid to the distal tip portion of the catheter, or to carry power to the imaging array (not shown) of the SSID. As will be appreciated, imaging fluid could also be conveyed to the imaging site via another lumen 114 or a guiding catheter, or a completely separate catheter (not shown).

In another configuration state, shown in FIG. 9, the deformable outer sleeve 102 is bent, enabling direct viewing forwardly through the opening 106. Also, views rearwardly at various angles can be obtained by causing more or less deflection of the deformable outer sleeve 102. Attached to the tube adjacent one side (a bottom side in FIG. 9), a tension wire 78 deflects the deformable outer sleeve as tension is applied. Another way for deforming the sleeve is to form it from a NiTi alloy, which changes shape from a first configuration shown in FIG. 8 to a second configuration in FIG. 9 via change of temperature such as can be affected by introduction of imaging fluid of a different temperature, or by running an electrical current therethrough. In the latter two embodiments, the tip has essentially two states, deformed and undeformed.

Referring now to FIG. 10, a system, indicated generally at 120, includes a GRIN lens 40 and an SSID 38. The SSID can comprise a silicon or silicon-like substrate or amorphous silicon thin film transistors (TFT) 126 having features typically manufactured therein. Features including the imaging array 122, the conductive pads 42, metal traces (not shown), circuitry (not shown), etc., can be fabricated therein. With respect to the conductive pads, the connection between conductive pads and a conductive line of an umbilical (not shown) can be through soldering, wire bonding, solder bumping, eutectic bonding, electroplating, and conductive epoxy. However, a direct solder joint having no wire bonding between the electrical umbilical and the conductive pads can be preferred as providing good steerability can be achieved with less risk of breaking electrical bonding. In one embodiment, the conductive line of the umbilical can provide power, ground, clock signal, and output signal with respect to the SSID. Other integrated circuit components can also be present for desired applications, such as light emitting diodes (LEDs) 124, for providing light to areas around the GRIN lens.

It is not required that all of these components be present, as long as there is a visual data gathering and sending image device present, and some means provided to connect the data gathering and sending device to a visual data signal processor. Other components, such as the umbilical, housing, adaptors, utility guides, and the like, can also be present, though they are not shown in FIG. 10. The SSID 38 can be any solid state imaging device, such as a CCD, a CID, or a CMOS imaging device. Also shown, the GRIN lens 40 is coated with an opaque coating 128 on the curved surface to prevent light from entering the lens at other than the flat surface that is most distal with respect to the SSID.

FIG. 11 depicts an alternative system 130 that includes multiple imaging arrays 122a, 122b, 122c on a common SSID 38. Though only three imaging arrays are shown in this perspective view, five imaging arrays are present in this embodiment (i.e., one on each side of five sides the substrate 126, with the back side of the substrate providing a surface for umbilical connection). Each imaging array is respectively optically coupled to a GRIN lens 40a, 40b, 40c, 40d, 40e. As can be appreciated, this is but one configuration where multiple imaging arrays with multiple GRIN lenses can be used. Fewer or more imaging arrays can be used in other similar embodiments, and/or can be part of multiple SSIDs. Umbilical connections are not shown, though it is understood that an umbilical can be present to operate the SSID and its multiple imaging arrays (either by signal splitting or by the use of separate power and/or signal sources).

FIG. 12 depicts a system, shown generally at 140, which can provide stereoscopic imaging. Specifically, multiple imaging arrays 122a, 122b, are shown on a common SSID 38 in a coplanar arrangement. A pair of GRIN lenses 40a, 40b are shown as they would be optically coupled to imaging arrays 122a, 122b, respectively. Other than the imaging array, other features are also present in the SSID, including conductive pads 42 for providing an electrical connection to an umbilical (not shown).

Figure 18:
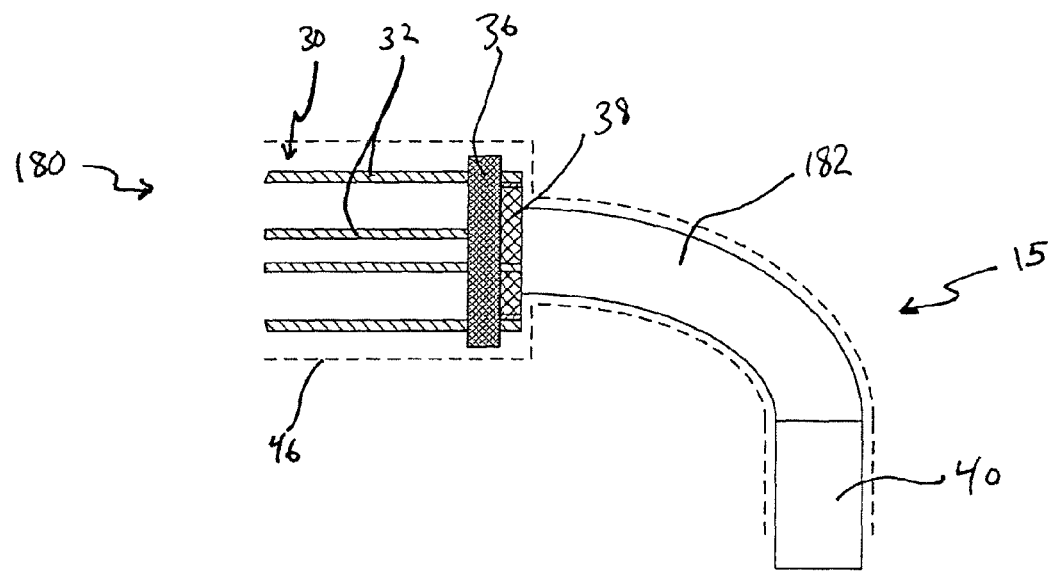
FIG. 18 is a schematic side view representation of another exemplary embodiment having a fiber optic inserted therein.

Referring now to FIG. 13, a system 110 includes multiple microcameras 120a, 120b, 120c positioned along an umbilical 30, which are attached to conductive wires 32 of the umbilical. The umbilical includes a proximal end 184, which can be coupled to a processor/monitor (not shown) for viewing, and a distal end 186. Each microcamera includes an SSID 38 and a GRIN lens 40. In the embodiment shown, the microcamera 120c that is closest to a terminal end 186 is optically coupled to a fiber optic line 182, which can include a GRIN lens at a terminal end of the fiber optic line, as shown in FIG. 18 below. However, the microcamera closest to the terminal end can actually be at a distal tip of the catheter. To illustrate an approximation of the size of the microcameras of the present invention, structure 188 is shown, which is approximately the size of a small coin, such as a United States dime.

The embodiments thus far shown depict GRIN lenses optically coupled to imaging arrays of SSIDs by a direct bonding or coupling. However, the term "optically coupled," also provides additional means of collecting light from GRIN lens and coupling it to an imaging array of an SSID. For example, other optical devices can be interposed between a GRIN lens and an SSID, such as a color filter, fiber optic, or any shape optical lens including a prism or wide angle lens. Specifically, a system of converting monochrome imaging to multiple colors can be accomplished by utilizing a filter having a predetermined pattern, such as a Bayer filter pattern. The basic building block of a Bayer filter pattern is a 2×2 pattern having 1 blue (B), 1 red (R), and 2 green (G) squares. An advantage of using a Bayer filter pattern is that only one sensor is required and all color information can be recorded simultaneously, providing for a smaller and cheaper design. In one embodiment, demosaicing algorithms can be used to convert the mosaic of separate colors into an equally sized mosaic of true colors. Each color pixel can be used more than once, and the true color of a single pixel can be determined by averaging the values from the closest surrounding pixels.

Figure 14:
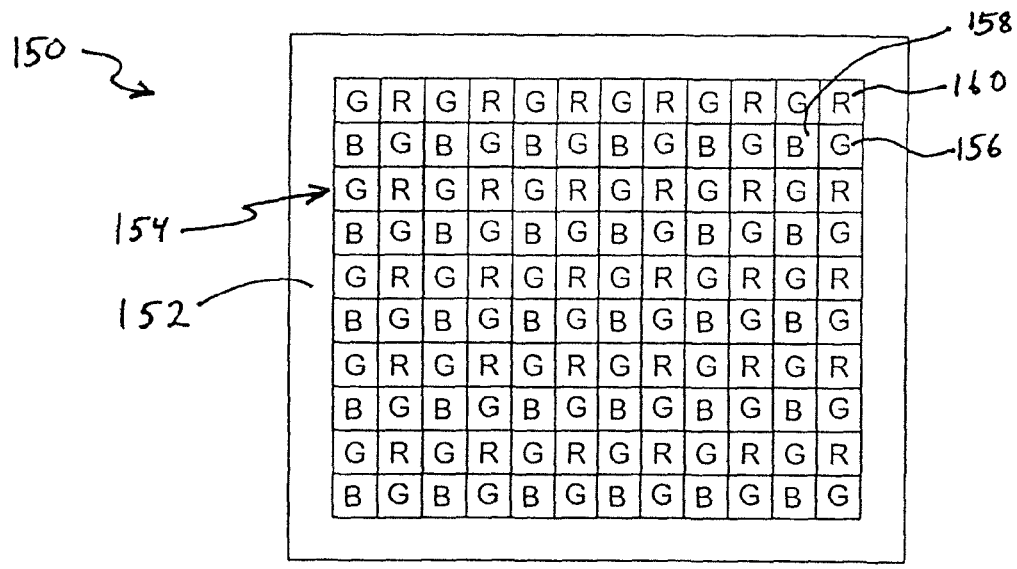
FIG. 14 is plan view along the optical axis of an exemplary color filter insert that can be used with imagine devices in accordance with principles of the invention.
Figure 15:
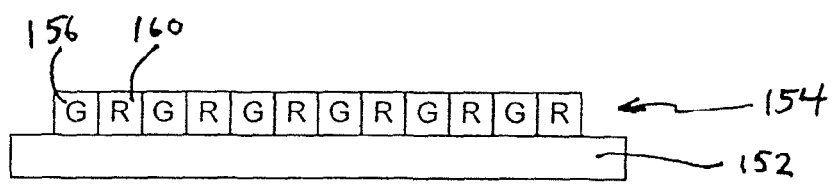
FIG. 15 is a first side view of the color filter insert of FIG. 14.
Figure 16:
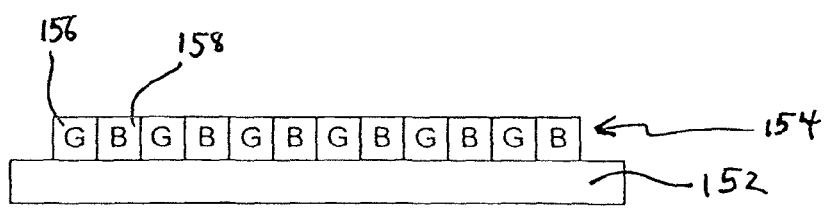
FIG. 16 is a second side view of the color filter insert of FIG. 14, taken at 90 degrees with respect to FIG. 15.

Specifically, with reference to FIG. 14-16, a color filter insert, shown generally at 150, can comprise a substantially optically clear filter substrate 152 and a color filter mosaic portion 154. The filter insert as a whole is made up of green transparent color material 156, blue transparent color material 158, and red transparent color material 160. Each of the transparent color material 156, 158, 160 can be polymerized color resins such as those available from Brewer Science. In one embodiment, the green color material 156 can be put down on the clear filter substrate first, and then the red 160 and blue 158 color material can be positioned in the appropriate spaces provided by the green material. Each transparent color material can be configured to be the size of an SSID image array pixel. The optically clear filter substrate can be, for example, a polymeric material such as SU-8 available from IBM, having a thickness of about 20 microns, though other thicknesses and materials can be used.

Figure 17:
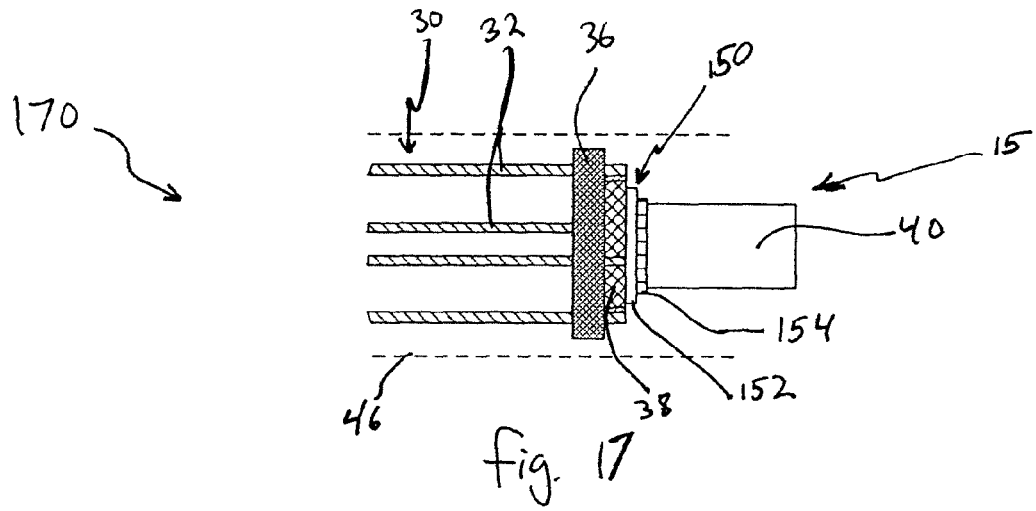
FIG. 17 is a schematic side view representation of another exemplary embodiment having a color filter insert of FIG. 14 inserted therein.

Turning now to FIG. 17, a system 170, including a color filter insert 150 having an optical clear filter substrate 152 and the color filter mosaic portion 154, can be positioned between a GRIN lens 40 and an imaging array (not shown) of an SSID 38. FIG. 18 depicts an alternative system 180, wherein a fiber optic 182 is used to optically couple a GRIN lens 40 with an imaging array (not shown) of an SSID 38. Any bonding technique or mechanical coupling can be used to connect the SSID to the GRIN lens through the color filter insert or fiber optic in order to make the optical connection, such as bonding by an optically clear bonding epoxy. In both FIGS. 17 and 18, as described previously, the imaging device at the distal tip 15 can include a utility guide 36 for supporting or carrying the umbilical 30, which can include electrical wires 32 and other utilities (not shown). Both FIGS. 17 and 18 also depict micro-machined tubing 46 to support and direct the camera.

As will be appreciated, an imaging device in accordance with principles of the invention can be made very small, and is useful in solving certain imaging problems, particularly, that of imaging a remote location within or beyond a small opening, for example in human anatomy distal of a small orifice or luminal space (anatomical or artificial, such as a trocar lumen), or via a small incision, etc. In fact, because of the solid state nature of the SSID, and because of the use of the GRIN lens, these cameras can be made to be micron-sized for reaching areas previously inaccessible, such as dental/orthodontics, fallopian tubes, heart, lungs, vestibular region of ear, and the like. Larger lumens or cavities can be view with a greater degree of comfort and less patient duress, including the colon, stomach, esophagus, or any other similar anatomical structures. Additionally, such devices can be used for in situ tissue analysis.

It is to be understood that the above-referenced arrangements are illustrative of the application for the principles of the present invention. Numerous modifications and alternative arrangements can be devised without departing from the spirit and scope of the present invention while the present invention has been shown in the drawings and described above in connection with the exemplary embodiments(s) of the invention. It will be apparent to those of ordinary skill in the art that numerous modifications can be made without departing from the principles and concepts of the invention as set forth in the claims.

The invention claimed is:

1. A miniaturized imaging device, comprising:
a catheter having proximal end and a distal end, the distal end of said catheter comprises a deformable tip, the deformable tip comprising:
at least one opening about a lateral side of the tip;
a solid state imaging chip disposed at a distal end of the catheter;
a lens system optically coupled to the solid state imaging chip;
a mirror element fixedly disposed within a distal end of the deformable tip and oriented to reflect light entering the deformable tip through the at least one opening directly towards the lens system; and
an adjustable imaging field of view created by movement of the deformable tip and mirror element with respect to the lens system.

2. The imaging device of claim 1, wherein the lens system is oriented substantially collinear with the mirror element when the deformable tip is disposed in an unbiased position.

3. The imaging device of claim 1, wherein a field of view of the imaging device is at least partially rearward of the lens system when the deformable tip is disposed in an unbiased position.

4. The imaging device of claim 1, further comprising a first imaging field of view when the deformable tip is disposed in an unbiased position and a second imaging field of view when the deformable tip is disposed in a biased position.

5. The imaging device of claim 1, wherein a field of view of the imaging device is adjustable dependent upon the position of the deformable tip relative to a longitudinal axis of the catheter.

6. The imaging device of claim 1, wherein a field of view of the imaging device is approximately 25 to 50 degrees rearward of the lens system, with respect to the longitudinal axis of the catheter, when the deformable tip is disposed in an unbiased position.

7. The imaging device of claim 1, wherein a field of view of the imaging device is at least partially forward of the lens system when the deformable tip is disposed in a biased position.

8. The imaging device of claim 1, wherein a proximal end of the at least one lateral opening is adjacent a distal end of the lens system.

9. The imaging device of claim 1, wherein the deformable tip is laterally deformable relative to a longitudinal axis of the catheter.

10. A miniaturized imaging device, comprising:
a catheter having a proximal end and a distal end;
a solid state imaging chip disposed near a distal end of the catheter;

a lens system optically coupled to the solid state imaging chip;

a deformable tip having an opening about a lateral side of the tip and a mirror element fixedly disposed within a distal end of the deformable tip and oriented to reflect light entering the deformable tip through the at least one lateral opening directly towards the lens system to create an imaging field of view which is:

a. at least partially rearward of the lens system when the deformable tip is disposed in a first position with respect to the lens system;

b. at least partially lateral of the lens system when the deformable tip is disposed in a second position with respect to the lens system; and c. at least partially forward and partially rearward of the lens system when the deformable tip is disposed in a third position with respect to the lens system.

11. The miniaturized imaging device of claim 10, further comprising a tensioning device adapted to deform the deformable tip.

12. The miniaturized imaging device of claim 10, further comprising a shape memory alloy disposed within the deformable tip and adapted to move the deformable tip from an unbiased position to a biased position.

13. A method of imaging a target within a body, comprising:

advancing a catheter into a portion of the body, said catheter comprising a deformable tip, and at least one opening about a lateral side of the tip, a solid state imaging chip disposed at a distal end of the catheter, a lens system optically coupled to the solid state imaging chip, and a mirror element fixedly disposed within a distal end of the deformable tip;

disposing the deformable tip in an unbiased position such that a field of view of the imaging chip is at least partially rearward of the lens system;

propagating a wavelength of light onto the target;

receiving a wavelength of light reflected from the target to the mirror element; and receiving a wavelength of light reflected directly from the target mirror element to the lens system.

14. The method of claim 13, further comprising laterally moving the deformable tip relative to a longitudinal axis of the catheter such that a field of view of the imaging chip is at least partially lateral and partially rearward of the lens system.

15. The method of claim 13, further comprising laterally moving the deformable tip relative to a longitudinal axis of the catheter such that a field of view of the imaging chip is at least partially forward and partially rearward of the lens system.

16. The method of claim 13, further comprising laterally moving the deformable tip relative to a longitudinal axis of the catheter to adjust the field of view of the imaging chip.

17. The method of claim 13, wherein the deformable tip further comprises a shape memory material configured to maintain the deformable tip substantially collinear with a longitudinal axis of the catheter when the shape memory material is in an unbiased state.

18. The method of claim 17, further comprising injecting a fluid onto a shape memory material to laterally move the deformable tip.

19. The method of claim 17, further comprising conducting a current of electricity through the shape memory material to laterally move the deformable tip.

20. The method of claim 13, wherein the lens system comprises a GRIN lens attached directly to the solid state imaging chip.

* * * * *